US006083728A

United States Patent [19]
Schendel et al.

[11] Patent Number: 6,083,728
[45] Date of Patent: Jul. 4, 2000

[54] PRODUCTION OF GLUTAMATE USING WILD TYPE *BACILLUS METHANOLICUS*

[75] Inventors: Frederick J. Schendel, Oakdale; Richard Dillingham, Minneapolis; Richard S. Hanson, Wayzata, all of Minn.; Konosuke Sano; Kazuhiko Matsui, both of Kawasaki, Japan

[73] Assignee: Regents of the University of Minnesota, Minneapolis, Minn.

[21] Appl. No.: 08/953,265

[22] Filed: Oct. 17, 1997

[51] Int. Cl.$^7$ .............................. C12P 13/14; C12N 1/20
[52] U.S. Cl. ..................... 435/110; 435/252.5; 435/832
[58] Field of Search ................................ 435/110, 252.5, 435/832

[56] References Cited

U.S. PATENT DOCUMENTS

| Re. 30,965 | 6/1982 | Hitzman | 435/68 |
|---|---|---|---|
| 3,212,994 | 10/1965 | Kono et al. | 195/29 |
| 3,359,178 | 12/1967 | Tanaka et al. | 195/28 |
| 3,563,857 | 2/1971 | Oki et al. | 195/49 |
| 3,663,370 | 5/1972 | Kono et al. | 195/49 |
| 3,707,441 | 12/1972 | Shiio et al. | 195/49 |
| 3,939,042 | 2/1976 | Nakayama et al. | 195/49 |
| 3,981,774 | 9/1976 | Hitzman | 195/49 |
| 4,411,991 | 10/1983 | Hirakawa et al. | 435/42 |
| 4,652,527 | 3/1987 | Stirling | 435/253 |
| 5,250,434 | 10/1993 | Yamada et al. | 435/252.1 |

FOREIGN PATENT DOCUMENTS

| 1579160 | 8/1969 | France . |
|---|---|---|
| 49-34837 | 9/1974 | Japan . |
| 57-14839 | 3/1982 | Japan . |
| 62-48393 | 3/1987 | Japan . |
| 732377 | 5/1980 | U.S.S.R. . |
| 0826097 | 12/1959 | United Kingdom . |
| WO 90/12105 | 10/1990 | WIPO . |

OTHER PUBLICATIONS

Akiba, T. et al., "Identifications of Lower Alcohol–Utilizing Bacteria," *J. Ferment. Technol.*, 48(6):323–328 (1970).
Al–Awadhi, N. et al., "Growth characteristics of a thermotolerant methylotrophic Bacillus sp. (NCIB 12522) in batch culture," *Appl. Microbiol. Biotechnol.*, 29:485–493 (1988).
Anthongy, C., "The Biochemistry of Methylotrophs," *Academic Press*, London, p. 3 (1982).
Arfman, N. et al., "*Bacillus methanolicus* sp. nov., a New Species of Thermotolerant, Methanol–Utilizing, Endospore– Forming Bacteria," *Intl. J. Syst. Bacteriology*, 42(3):439–445 (Jul. 1992).
Austin, G. et al., "Control of Methanol Concentration Using an On–Line Methanol Sensor," American Chemical Society National Meeting, Toronto, Ontario, Canada, 1 page (Jun. 1988).
Bohanon, M. J. et al., "Isolation of Auxotrophic Mutants of Methylophilus methylotrophus by Modified–Marker Exchange," *Appl. Environ. Microbiol.*, 54(1):271–273 (Jan. 1988).

Brooke, A. G. et al., "Environmental control of metabolic fluxes in thermotolerant methylotrophic Bacillus strains," *Arch. Microbiol*, 151:268–273 (1989).
Clement, W. et al., "Isolation and Characterization of Methanol–Utilizing Thermotolerant Bacteria," Abstracts of the Fifth International Symposium of Microbial Growth on $C_1$ Compounds, p. 69 (Free Univ. Press, Amsterdam, Aug. 11–16, 1986).
Cox, R. et al., "Hexose Phosphate Synthase in Trimethylamine–Grown Bacterium 2B2, a Facultative Methylotrop," *Biochem. J.*, 141:605–608 (1974).
de Vries, G. E., "Molecular biology of bacterial methanol oxidation," *FEMS Microbiol. Rev.*, 39:235–258 (1986).
de Vries, G. E. et al., "Physiology and genetics of methylotrophic bacteria," *FEMS Microbiol. Rev.*, 75:57–101 (1990).
Dijkhuizen, L. et al., "Isolation and initial characterization of thermotolerant methylotrophic Bacillus strains," *FEMS Microbiol. Lett.*, 52:209–214 (1988).
Doetsch, R., "Determinative Methods of Light Microscopy," in Manual of Methods for General Bacteriology, *American Society for Microbiology*, pp. 22–33 (1981).
Gerhardt, P. et al., Editors, Manual of Methods for General Bacteriology, *American Society for Microbiology*, pp. 230–231 (1981).
Gregersen, T., "Rapid Method for Distinction of Gram–Negative from Gram–Positive Bacteria," *Eur. J. Appl. Microbiol. Biotechnol.*, 5:123–127 (1978).
Guettler, M. et al., "Characterization of a Methanol Oxidizing Thermophilic Member of the Genus Bacillus," report the isolation of strain MGA3, the morphological variant strain Gr, and the tyrosine–requiring mutant N4 of MGA3. This material was presented as a poster presentation at the 88$^{th}$ Annual Meeting of the American Society for Microbiology, Wednesday, May 11, 1988. The Abstract only was published Mar. 16, 1988.
Haber, C. L. et al., "Methylotrophic Bacteria: Biochemical Diversity and Genetics," *Science*, 221:1147–1153 (Sep. 16, 1983).
Hagino, H. et al., "L–Lysine Production by Mutants of *Bacillus Licheniformis*," *Biotech. Letters*, 3(8):425–430 (1981).
Hanson, R. S. et al., "Ecology and Diversity of Methylotrophic Organisms," *Adv. Appl. Microbiol.*, 26:3–39 (1980).
Harms, N. et al., "Isolation and Nucleotide Sequence of the Methanol Dehydrogenase Structural Gene from *Paracoccus denitrificans*," Journal of Bacteriology, 169(9):3969–3975 (Sep. 1987).

(List continued on next page.)

Primary Examiner—Irene Marx
Assistant Examiner—Vera Afremova
Attorney, Agent, or Firm—Merchant & Gould P.C.

[57] ABSTRACT

A method of producing glutamic acid by culturing a biologically pure wild type Bacillus methanolicus which exhibits sustained growth at 50° C. using methanol as a carbon and energy source and requiring vitamin $B_{12}$ and biotin is provided.

23 Claims, 6 Drawing Sheets

OTHER PUBLICATIONS

Hazeu, W. et al., "Nocardia sp. 239, a facultative methanol utilizer with the ribulose monophosphate pathway of formaldehyde fixation," *Arch. Microbiol.*, 135:205–210 (1983).

Holloway, B. W., "Genetics of Methylotrophs," in *Methylotrophs: Microbiology, Biochemistry and Genetics*, C. T. Hou, ed., CRC Press, Boca Raton, FL, pp. 87–104 (1984).

Holloway, B. W. et al., "The Molecular Genetics of $C_1$ Utilizing Microorganisms, An Overview," *Microbial Growth on $CH_1$ Compounds*, H. W. Van Verseveld and J. A. Duine, eds., Martinus Nyhoff, Dordrecth, pp. 223–229 (1987).

Janssen, F. W. et al., "Colorimetric Assay for Dipicolinic Acid in Bacterial Spores," *Science*, 127:26–27 (1958).

Large, P. J. et al., "Microbial Growth on $C_1$ Compounds," *Biochem. J.*, 87:386–396 (1963).

Laskin and Lechevalier, *CRC Handbook of Microbiology*, vol. I, CRC Press, pp. 734–735 (1971).

Linton, J. D. et al., "The Potential of One–Carbon Compounds as Fermentation Feedstocks," *Microbial Growth on $C_1$ Compounds*, H. W. van Verseveld and J. S. Duine, eds., Martinus Nyhoff, Dordrecht, pp. 263–271 (1987).

Machlin, S. M. et al., "Genetic and Physical Analyses of *Methylobacterium organophilum* XX Genes Encoding Methanol Oxidation," *Journal of Bacteriology*, 170(1):141–148 (Jan. 1988).

Mandel, M. et al., "Use of Ultraviolet Absorbance–Temperature Profile for Determining the Guanine Plus Cytosine Content of DNA," *Methods Enzymol.*, 12:195–206 (1968).

Mimura, A. et al., "Isolation and Characterization of a Gram–positive Methanol Assimilating Bacterium," *J. Ferment. Technol.*, 56(4):243–252 (1978).

Motoyama, H. et al., "Amino Acid Production from Methanol by *Methylobacillus glycogenes* Mutants: Isolation of L–Glutamic Acid Hyper–producing Mutants from *M. glycogenes* strains, and Derivation of L–Threonine and L–Lysine–producing Mutants from Them," *Biosci. Biotech. Biochem.*, 57(1):82–87 (1993).

Nicolaidis, A. A. et al., "Isolation of methane monooxygenase–deficient mutants from *Methylosinus trichosporium* OB3b using dichloromethane," *FEMS Microbiology Letters*, 41:47–52 (1987).

Nunn, D. N. et al., "Phenotypic Characterization of 10 Methanol Oxidation Mutant Classes in Methylobacterium sp. Strain AM1," *Journal of Bacteriology*, 166(2):591–597 (1986).

Rogers, H. J. et al., "The Isolation and Characterization of Mutants of *Bacillus subtillis* and *Bacillus licheniformis* with Disturbed Morphology and Cell Division," *Journal of General Microbiology*, 61:155–171 with 12 plates (1970).

Schendel, F. J. et al., "L–Lysine Production from Methanol at High Cell Densities of MGA3, a Thermophilic Bacillus," Abstract from 1989 ASM Annual Meeting (published Mar. 21, 1989).

Schendel, F. J. et al., "L–Lysine Production at 50° C. by Mutants of a Newly Isolated and Characterized Methylotrophic Bacillus sp.," *Applied and Environmental Microbiology*, 56(4):963–970 (Apr. 1990).

Program of the 89th Annual Meeting of the American Society for Microbiology p. 193 lists the title for the following poster session: No. 0 69, F. J. Schendel et al., "L–Lysine Production from Methanol at High Cell Densitites of MGA3, a Thermophilic Bacillus sp." This program was made available to meeting registrants as of Mar. 21, 1989.

Shiio, I., "Tryptophan, Phenylalanine, and Tyrosine," pp. 188–206 (1986).

Simon, R. et al., "A Broad Host Range Mobilization System for In Vivo Genetic Engineering: Transposon Mutagenesis in Gram Negative Bacteria," *Bio/Technology*, 1:784–791 (1983).

Sonnleitner, B. et al., "Advantages of using thermophiles in biotechnological processes: expectations and reality," *Trends in Biotechnology*, 1(3):74–80 (1983).

Snedecor, B. et al., "Thermophilic Mixed Culture of Bacteria Utilizing Methanol for Growth," *Applied Microbiology*, 27(6):1112–1117 (1974).

Tosaka, O. et al., "The production of L–lysine by fermentation," *Trends in Biotechnology*, 1(3):70–74 (1983).

Tosaka, O. et al., "Lysine," in *Progress in Industrial Microbiology*, 24, K. Aida et al., eds., pp. 152–172 (1986).

Whittenbury, R. et al., "Exospores and Cysts Formed by Methane–utilizing Bacteria," *Journal of General Microbiology*, 61:219–226 (1970) with 5 plates.

Work, E. "Reaction of Ninhydrin in Acid Solution with Straight–Chain Amino Acids Containing Two Amino Groups and its Application to the Estimation of $\alpha\epsilon$–Diaminopimelic Acid," *Bioch.*, 67:416–423 (1957).

Hur, T. et al., "Amino Acid Production from Methanol at 50° C. by *Bacillus Methanolicus* During Growth Controlled", Abstracts of the General Meeting of the American Society for Microbiology, vol. 93, p. 319, (1993), XP–002090259.

Motoyama, H. et al., "Production of Amino Acids by Methanol–Utilizing Bacteria", Chemical Abstracts, vol. 126, No. 15, Apr. 14, 1997, XP–002091946.

Pluschkell, S. B. et al., "Growth and Glutamic Acid Production by *Bacillus Methanolicus* MGA3", Book of Abstracts, 216th ACS National Meeting, Boston, Aug. 23–27, 1998, XP–002091947.

Pluschkell, S. B. et al., "Growth and Glutamic Acid Production by *Bacillus Methanolicus* MGA3", Book of Abstracts, 216th ACS National Meeting, Boston, Aug. 23–27, 1998, XP–002091948.

Nico Arfman, "Methanol Metabolism in Thermotolerant Bacilli", Rijksuniversiteit Groningen, pp. 1–183 (Aug. 30, 1991).

Lee et al., "Lysine production from methanol at 50 C using *Bacillus methanolicus:* modeling volume control, lysine concentration, and productivity using a three–phase continuous simulation", Biotechnology and Bioengineering, 1996, vol. 49, pp. 639–653.

Hanson et al., "Production of L–Lysine and some other amino acids by mutants of *Bacillus methanolicus*", Microb. Growth C1 Compd., Proc.Int.Symp., 8th (1996), meeting Date 1995, 227–236. Edtor(s): Lidstrom, Mary E.; Tabita, F. Robert. Kluwer: Dordrecht.

… … … … … … … … … … … … … … … … … … … … … … … … … … … … … …

PRODUCTION OF GLUTAMATE USING WILD TYPE *BACILLUS METHANOLICUS*

BACKGROUND OF THE INVENTION

This invention relates to production of glutamate using wild type *Bacillus methanolicus*.

Microorganisms that utilize one-carbon compounds more reduced than carbon dioxide (methylotrophs) are diverse and ubiquitous. Anthony, *The Biochemistry of Methylotrophs*, page 3 (Academic Press, London 1982); Hanson, *Adv. Appl. Microbiol.*, 26:3 (1980). Those methylotrophic bacteria reported to utilize methane are all gram-negative and nearly all have an obligate requirement for one-carbon compounds as energy sources. Anthony, supra; Whittenburg et al. *J. Gen. Microbiol.*, 61: 219–226 (1970). Bacteria that grow on methanol and methylamines but not methane include several facultative as well as obligate methylotrophs. Anthony, supra; Hanson, supra. All the obligate methylotrophs unable to utilize methane are gram-negative aerobic bacteria. Anthony, supra.; Whittenburg, supra. Of the facultative methylotrophs isolated that utilize methanol, methylamine or both, only a few were gram positive and were assigned to the genera Bacillus, Corynebacterium, Arthrobacter, or Nocardia. Akiba et al, *J. Ferment. Technol.*, 48:323–328 (1970); Clement et al. *Abstracts of the Fifth International Symposium Microbiol. Growth on $C_1$ Compounds*, p. 69 (Free Univ. Press, Amsterdam 1986); Hazen et al, *Arch. Microbiol.*, 135:205–210 (1983); Mimura et al., *J. Ferment. Technol.*, 5:243–252 (1978).

Some species of facultative gram positive methyltrophs that utilize methanol, methylamine or both have now been classified together and named *Bacillus methanolicus*. Arfman et al., *Int. J. System. Bact.*, 42:438 (1992). Characteristics of *Bacillus methanolicus* are identified in Arfman et al., cited supra.

The industrial advantages of a thermophilic methanol utilizing fermentation process at elevated temperatures have been described, Snedecor and Cooney, *Appl. Microbiol.*, 22:112–1117 (1974). For example, use of elevated temperatures can significantly reduce cooling costs. Use of methanol as a carbon and energy source is cost efficient because of its wide availability and low cost. A methanol utilizing, thermophilic mixed culture that included an endospore-forming species was selected by Snedecor and Cooney; however, Snedecor and Cooney, were unable to isolate a pure culture capable of growth on methanol. It is extremely difficult or impossible to isolate appropriate wild type strains from mixed or impure cultures.

Large scale production of glutamic acid is desired for many commercial applications. For example, glutamic acid is used in the production of moisturizers in cosmetics, gelatinizing agents in vegetable oils, for oil dispersion, and as a seasoner for foods. The demand for monosodium glutamate exceeds 300,000 tons per year. To date no production of amino acids, such as glutamic acid, using an isolated wild type Bacillus species capable of rapid growth on methanol at temperatures above 50° C. has occurred.

Accordingly, there is a need for a method of producing glutamic acid using a wild type *Bacillus methanolicus* which exhibits sustained growth on methanol at a temperature of at 50° C. There is also a need for an inexpensive method of producing glutamic acid on an industrial scale.

SUMMARY OF THE INVENTION

The invention provides using microorganisms in a method for producing glutamic acid. The method involves culturing wild type *Bacillus methanolicus* in media with methanol as a carbon source and recovering glutamate from the nutrient media. In one embodiment, *Bacillus methanolicus* culture is in medium including a copper ion and biotin at a cell density of more than about 20 g/L cell dry weight at a temperature of about 45° C. to about 60° C. until glutamate is produced at a concentration of at least about 20 g/L, preferably more than about 25 g/L. In another embodiment, *Bacillus methanolicus* culture is in medium including a limiting amount of magnesium ion at a temperature of about 45° C. to about 60° C. until glutamic acid is produced at a concentration of at least about 20 g/L, preferably more than about 25 g/L. The method is especially useful to produce glutamate on an industrial scale from an inexpensive and readily available substrate such as methanol. In one embodiment the media also includes a surfactant.

Strains of *Bacillus methanolicus* used in the invention have the following characteristics: (1) gram positive; (2) spore forming with spores present at central to subterminal location; (3) obligate aerobic growth at temperatures of about 35° C. to about 60° C. with optimal growth at about 55° C.; (4) exhibits sustained growth on methanol; (5) utilizes a ribulose monophosphate pathway to convert methanol to carbon dioxide; and (6) has a G/C content of about 44% to about 52%.

According to the invention, the wild type strain *Bacillus methanolicus* exhibits sustained growth at 50° C. in nutrient media comprising methanol as a carbon source and produces glutamate at a concentration of at least about 20 g/l. More preferably the wild type strain produces about 25 to about 100 g/l glutamate, and most preferably about 30 to about 70 g/l glutamate. Using the invention, carbon conversion of methanol to glutamate is at least about 20%.

In the preferred version, glutamate is produced by growth of a wild type strain of *B. methanolicus* under fed-batch or semi-continuous culture conditions. The cell cultures reach sufficient cell density to enhance glutamate production. Preferably, cell densities for glutamate production are about 20 grams dry weight per liter or greater. Preferably, when magnesium ion is limiting, cell densities for glutamate production are about 10 grams dry weight per liter or greater. The cultures are grown until glutamate is produced at a concentration at least about 25 g/l.

DETAILED DESCRIPTION OF THE INVENTION

A. Isolation and Characteristics of *Bacillus methanolicus* Strains

Characteristics of strains of bacteria classified as *B. methanolicus* can be found in Arfman et al., *Int. J. Syst. Bact.*, 439 (1992), which is hereby incorporated by reference. Although fermentation of substrates can vary among the strains as shown by Arfman et al., there are several characteristics that identify a bacterium as a strain of *B. methanolicus*. These characteristics include: (1) the bacteria are gram positive; (2) the bacteria form spores at a subterminal to central position; (3) growth is obligately aerobic and occurs at temperatures 35–60° C., with optimum growth at 55° C.; (4) growth on methanol is exhibited; (5) utilizes a ribulose monophosphate pathway to convert methanol to carbon dioxide; and (6) has a G/C content of about 44% to about 52%. Many strains of *B. methanolicus* are rod shaped. Typically, strains of *B. methanolicus* are motile during part of their life cycle.

Figure 6:
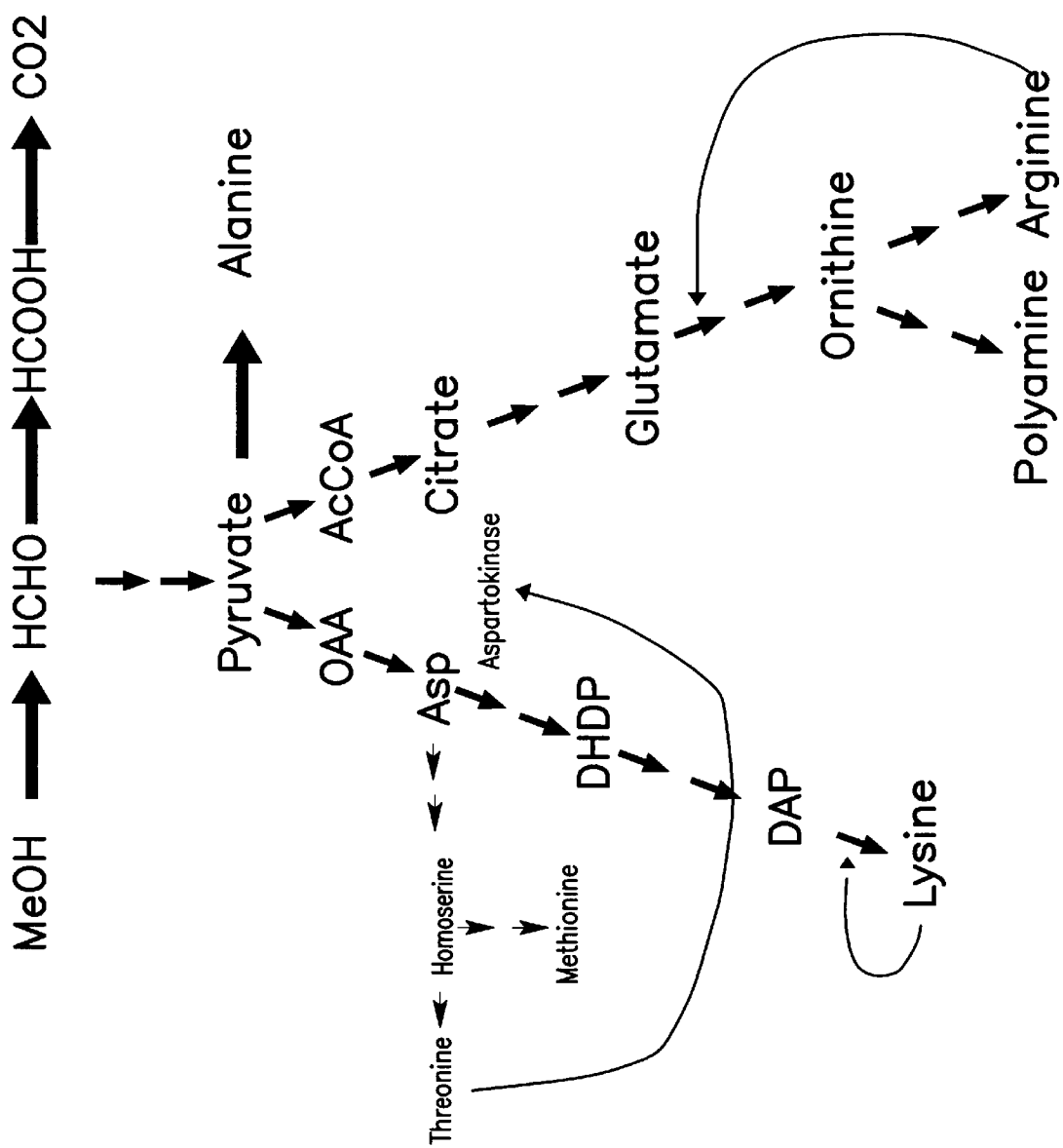
FIG. 6 shows the amino acid biosynthetic pathways employed by strains of *B. methanolicus*.

Characteristics of a preferred *Bacillus methanolicus* strain are that it is a gram positive, spore-forming rod that can grow at 50° C. in an aqueous nutrient media that includes methanol as a sole carbon and energy source with biotin and vitamin $B_{12}$ as required vitamins. The strains of *Bacillus methanolicus* are preferably isolated from environmental sources such as soil, dry soil, fresh water marsh soil, or bog muck. As stated above, *Bacillis methanolicus* used in the present invention are also characterized by utilization of an oxidative pathway that provides for conversion of methanol to $CO_2$ as shown in FIG. 6. This pathway also provides precursor compounds that can serve as building blocks for cellular components such as amino acids via the ribulose monophosphate pathway.

The invention can further employ *Bacillus methanolicus* strains characterized metabolically by amino acid synthetic pathways utilizing a methanol metabolite such as formaldehyde and as shown in FIG. 6. Briefly, methanol is converted to formaldehyde by an NADH linked methanol dehydrogenase that is uniquely present in this bacterium. Pyruvate, a product of the ribulose monophosphate pathway, serves as a precursor to the production of alanine, aspartic acid, lysine, glutamic acid, and arginine in three separate pathways.

The methylotrophic bacteria employed in the present invention include a strain of *Bacillus methanolicus*, preferably, having the characteristics as set forth in Table I, below.

TABLE I

Characteristics of Some Strains of *Bacillus methanolicus*

| | |
|---|---|
| Spore localization | subterminal |
| Survival after 10 min. at 80° C. | + |
| Sporulation at 37° C. | + |
| Optimum temperature for growth | 45–55° C. |
| Carbon and energy sources: | |
| Methanol | ++ |
| Mannitol | ++ |
| Glucose | + |
| Nitrogen Source: | |
| Ammonium | + |
| Nitrate | − |
| Nitrate reduction | − |
| Nitrate respiration | − |
| Hexulose phosphate synthase | + |
| DNA base ratios (moles % G + C) | 44–52 |

Figure 1:
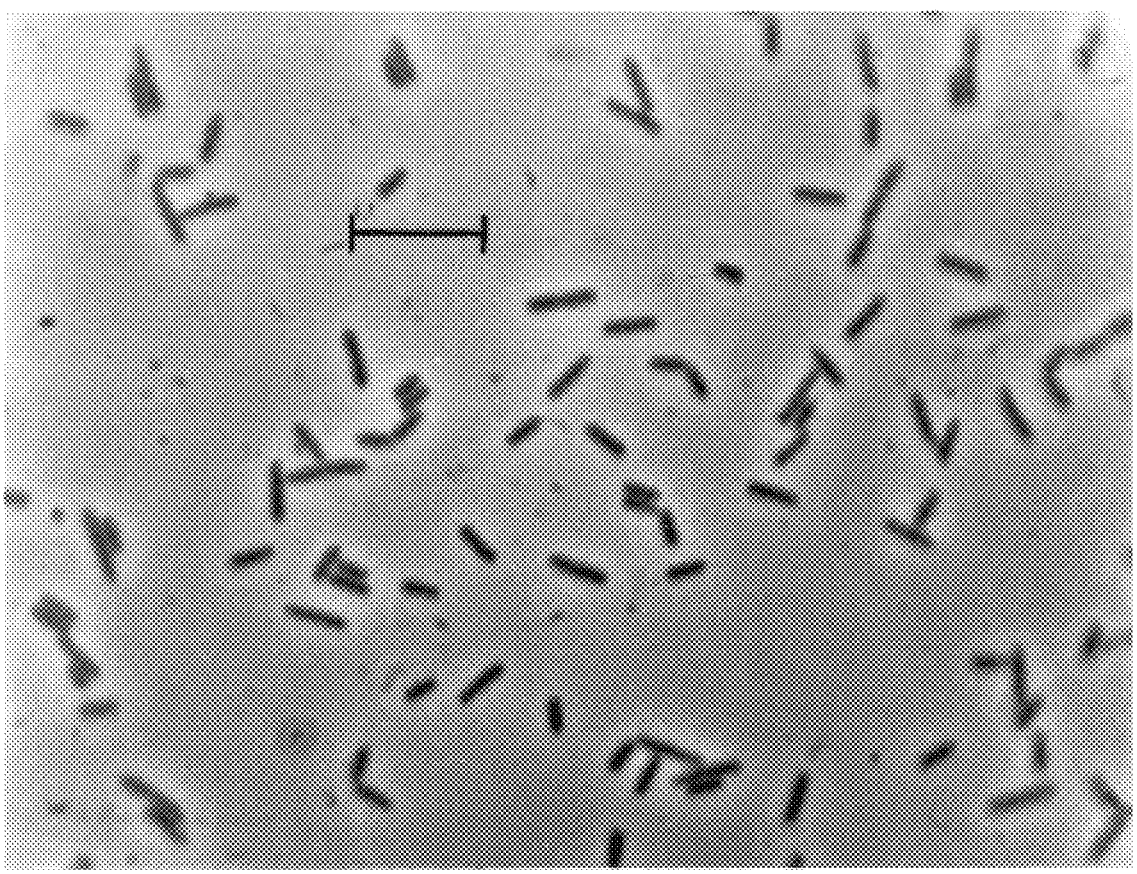
FIG. 1 is a phase contrast photomicrograph of strain MGA3 grown on MV medium at 53° C. The bar indicates 10 μm.

One preferred example of a bacteria used in the invention includes *B. methanolicus* strain MGA3. *B. methanolicus* strain MGA3 isolated in the manner described herein, from fresh water marsh soil, exhibited the characteristics indicated in Table I. The cell morphology is shown in FIG. 1. *B. methanolicus* MGA3 has been deposited with the American Type Culture Collection, 10801 University Boulevard, Manassas, Va. 20110–2209 on May 9, 1989, and given Accession No. 53907.

The present invention can also be practiced using "morphological variants" of *Bacillus methanolicus*. The term morphological variant is defined as individuals within a population or species that differ morphologically due to interaction between environmental influences and genotype. The term morphological variant is, in the case of one variant of *Bacillus methanolicus* MGA3, characterized by large pleomorphic cells occasionally visible in smears of strain MGA3 cultures.

Figure 2:
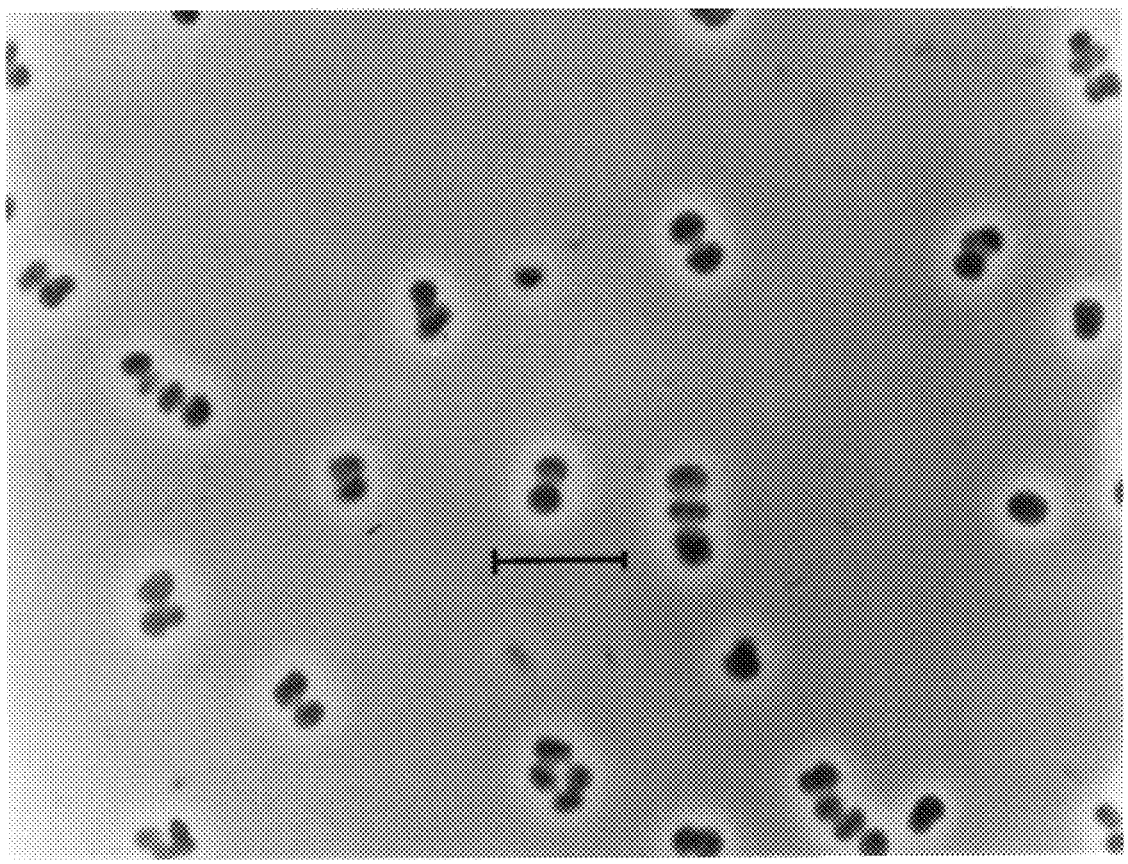
FIG. 2 is a phase contrast micrograph of strain Gr grown on MV medium at 45° C.

These pleomorphic cells were reminiscent of the pleomorphic cells seen in an original fermentor enrichment. A colony from a plate of MGA3 produced a pure culture of a morphological variant (FIG. 2). It was designated strain Gr. This strain shared most of the cultural and physiological characteristics of strain MGA3 that were tested. Strain Gr grew on methanol or mannitol at 50° C., was neutrophilic, required vitamin $B_{12}$ and biotin for growth, and resembled strain MGA3 in all other characteristics tested (Table I). Crude extracts of strain Gr also contained hexulose-phosphate-synthase activity. Strain Gr formed phase bright spores when a culture was switched from the non-permissive 53° C. to 37° C. A culture of strain Gr grown at high temperature did not survive heat inactivation but cells from a culture incubated an additional 18 hours at 37° C. survived 80° C. for 10 minutes.

The gross appearance of Gr was similar to the rod mutants of *Bacillus subtilis* and *Bacillus licheniformis* isolated by Rogers et al., *J. Gen. Microbiol.*, 61:155–171 (1970).

The invention can also employ designated *Bacillus methanolicus* strain NOA2 that was isolated from pasteurized bog muck. NOA2 was isolated from a different environmental source than *Bacillus methanolicus* strain MGA3 by the same method as *Bacillus methanolicus* strain MGA3, but grown as a batch culture at 37° C. Strain NOA2 exhibits the species characteristics described in Table I. *B. methanolicus* NOA2 has been deposited American Type Culture Collection 10801 University Boulevard, Manassas, Va. 20110–2209 on Jun. 3, 1999 and given Accession No. PTA-166.

The invention can be practiced using any number of strains of *Bacillus methanolicus*. The exemplified strains illustrate that various strains of *Bacillus methanolicus* produce glutamate according to the invention. One of skill in the art can practice the invention using any number of *Bacillus methanolicus* strains that are ribulose monophosphate pathway utilizing and gram positive; form spores at a subterminal to central position; grow at 35° C. to 60° C., with optimum growth at 55° C.; grow on methanol; and have a G/C content of about 44% to about 52%. Strains of *Bacillus methanolicus* have a highly conserved 16s RNA. Fewer than 10 bases of the 16s RNA typically vary between strains of *Bacillus methanolicus*.

Wild type strains of *Bacillus methanolicus* include strains isolated from natural or environmental sources, such as soil, dry soil, fresh water marsh soil, bog muck, or pasteurized bog muck and that have the characteristics described above. Wild type bacteria having the characteristics of the invention can include mutants of *B. methanolicus* strains that are not amino acid auxotrophic mutants. As used herein, amino acid auxotrophic mutant refers to *B. methanolicus* mutants requiring one or more amino acids for growth. Mutant refers to a sudden heritable change in the phenotype of a strain, which can be spontaneous or induced by known mutagenic agents, including radiation and various chemicals.

One of skill in the art can make high levels of glutamate with methanol as a carbon source using other type I methylotrophic bacteria of the genus Bacillus in addition to *Bacillus methanolicus*. The skilled art worker can, based on the characteristics described herein, recognize other methylotrophic bacteria of the genus Bacillus that can be employed to produce high levels of glutamate when grown on methanol at 35° C. to 60° C. using the teachings herein.

As described herein "aqueous nutrient media" refers to a water based composition including minerals and their salts necessary for growth of the bacterium used in the present invention. Preferred nutrient media contains an effective amount of a phosphate source, a nitrogen source, a sulfate source, calcium and trace elements. As described herein "trace elements" refers to elements essential for growth in trace concentrations i.e., minute fractions of 1 percent (1000 ppm or less). As indicated in Table I, the bacterium used in the present invention can utilize a number of carbon and energy sources for growth other than methanol; including glucose or mannitol; however the preferred carbon and energy source is methanol.

A satisfactory media for culturing the bacterium employed in the present invention is a minimal salts media, such as that described in Example 1 or the like. In a preferred embodiment, such as Example 1, minimal salts media to grow the bacterium used in the present invention includes from about 20 to about 500 mM ammonium sulfate; from about 10 to 125 mM potassium phosphate, from about 0.1–1.5 mM calcium chloride; and salts of magnesium, and the trace metals: iron, copper, manganese, zinc, molybdenum, borate and cobalt in concentrations as stated in Examples 4 and 5. The amount of methanol and vitamin $B_{12}$ needed for growth can vary. The amount of methanol in the media can range from about 0.05% wt/vol. to about 5% wt/vol., with amounts of from about 0.2% wt/vol. to about 0.5% wt/vol. preferred. The media should contain at least 0.05% wt/vol. methanol. The amount of vitamin $B_{12}$ in the aqueous media can range from about 0.5 µg/l to 2 mg/l, with amounts from about 1 µg/l to 1 mg/l preferred. Optimal growth of the bacterium takes place at 45–550° C. within a pH range of about 6.0–8.0. No growth occurs when the pH is 5.5. Growth requires biotin in amounts from about 20 µg/l to 20 mg/l. When grown in minimal salts media with methanol, vitamin $B_{12}$ and biotin the bacterium used in the present invention can grow at a rate from about 0.2 $hr^{-1}$ to about 1.5 $hr^{-1}$ at a temperature of about 50° C. to 60° C.

B. Method of Glutamate Production

To produce glutamic acid from wild type *Bacillus methanolicus*, the organism is cultured in an aqueous nutrient medium including methanol as a carbon source. In one embodiment the medium also includes a source of copper ion and biotin. Preferably, biotin is present in a greater than limiting amount, for example, greater than 60 µg/l. In another embodiment, the medium includes limiting concentrations of magnesium. The medium also contains vitamins, such as vitamin $B_{12}$, together with amounts of a phosphate source, a sulfate source, a nitrogen source, calcium and trace elements in amounts such as indicated in Examples 4 and 5. As previously described a satisfactory media is a minimal salts media, such as described in Example 1 or the like.

The amounts of methanol, copper, magnesium, biotin, and vitamin B12 needed for production of glutamic acid can vary. Methanol can range from about 0.05% wt/vol. to 5% wt/vol. with an amount of from about 0.3% to about 2% wt/vol. methanol preferred. Methanol concentrations can also be expressed in units of molarity. In molar units, methanol concentration is preferably about 20 mM to about 800 mM, preferably about 100 mM. Copper ion is typically present as $Cu^{2+}$, which can be provided, preferably, as $CuCl_2$, preferably at a concentration of more than about 1 mg/L. Magnesium ion, in one embodiment, is limited. That is, the concentration of magnesium ion is in a range where cell growth depends on the concentration of magnesium. Limited magnesium includes the absence of magnesium. Biotin can be present at concentrations that do not limit the growth of *B. methanolicus*. That is, the concentration of biotin is sufficient that increasing the concentration of biotin does not significantly increase the growth of cells. Preferably, the concentration of biotin is more than about 6 µg/L, more preferably more than about 20 µg/L. Vitamin $B_{12}$ can range from about 0.5 µg/l to about 2 mg/l. With amounts of about 1 µg/l to about 1 mg/l preferred. At a minimum, at least about 0.05% wt/vol. methanol, 0.1 mg/l vitamin $B_{12}$ and about 20 µg/l to about 20 mg/l biotin are needed for production of glutamic acid.

Controlling the concentration of oxygen in the media during culturing of *B. methanolicus* is also advantageous. Preferably, oxygen levels are maintained at about 10% to about 45% saturation. Sparging with air or with pure oxygen regulates the concentration of oxygen in the media.

In some embodiments of the invention, a surfactant in the media increases glutamate production. Tween 80, a trade name for a formulation of polyoxyethylene sorbitan monooleate, is a desirable surfactant of the polyoxyethylene sorbitan class of surfactants. Other formulations of polyoxyethylene sorbitan are effective to increase glutamate production as well. The concentration of surfactant affects glutamate production. Preferably, the Tween 80 or polyoxyethylene sorbitan monooleate concentration is about 1.5 to about 3 g/L, preferably about 2 g/L. Cetyltrimethyl ammonium bromide (CTAB), a cationic surfactant, is another desirable surfactant. Preferably CTAB is at a concentration of about 0.5 to about 5 mg/L, preferably about 2 mg/L.

Some microbes exhibit enhanced production or excretion of glutamic acid when penicillin is included in their culture medium. Wild type strains of *B. methanolicus* do not depend on penicillin for high levels of excretion or production of glutamic acid. In fact, one strain used in the invention exhibits diminished glutamate production in the presence of penicillin.

Control of the pH provides for optimal growth of the wild type strains used in the present invention as well as enhancing glutamate production. The pH of the culture can be monitored and controlled by standard methods known to those of skill in the art. Preferably the culture is maintained at a pH of about 5.5 to about 7.2, and more preferably at a pH of about 6.0 to about 6.8.

Many nitrogen sources can be used in the aqueous nutrient media, such as ammonium chloride, ammonium sulfate and ammonium nitrate. The preferred nitrogen sources are ammonia, ammonium chloride, or $(NH_4)_2So_4$ required in amounts of at least 20 mmoles/L.

Employing wild type *Bacillus methanolicus*, glutamate can be produced in substantial quantities. That is, quantities of glutamate from at least 20 g/l to about 100 g/l, and preferably from about 25 g/l to about 70 g/L. When magnesium ion is not limiting, significant glutamate production occurs in culture at high cell densities, such as densities greater than about 20 g/L cell dry weight. When magnesium ion is limiting, significant glutamate occurs in culture at cell densities greater than about 10 g/L cell dry weight. The present invention is believed useful to produce glutamate either singly or in combination with many of the 19 amino acids, including lysine, aspartic acid, and/or alanine. In one embodiment, wild type strains can produce from about 30 to about 70 g/l of glutamate. The yield of glutamate can also be expressed as a fraction of the carbon source that is converted to glutamate. For example, yield of glutamate can be expressed as carbon conversion of methanol to glutamate in percent. The carbon conversion of methanol is typically at least about 20%, preferably about at least 30% to about 50%, or more.

When cultivated on minimal salts media of the type described in Example 1, wild type *Bacillus methanolicus* strains can grow at cell densities up to about 60 g/l dry wt. In the presence of non-limiting concentrations of magnesium ion, glutamate production typically becomes significant at cell densities of about 20 g/L and above. In the presence of limiting concentrations of magnesium ion, glutamate production typically becomes significant at cell densities of about 10 g/L and above. Preferably, cell growth on minimal salts media with vitamin $B_{12}$, biotin, and methanol at temperatures between 45° C. and 55° C. can be at least 10–20 g/l (dry weight) and up to about 0.6 grams of cells per gram methanol. Cell densities of 30–50g/l (dry weight) with cell yields of about 0.53 grams cells per gram methanol have been observed.

Wild type *B. methanolicus* can produce glutamic acid when grown in batch culture. However, fed-batch or semi-continuous feed of methanol and trace elements enhances glutamic acid production. Glutamic acid production by wild type *B. methanolicus* can be further enhanced by using continuous culture methods in which trace elements are fed automatically. The pH is preferably maintained at a pH of about 5.5 to 7.2, more preferably about 6.0 to 6.8. Production of glutamate by wild type strains is maximized when the bacterium employed in the present invention is grown to the required cell densities by using continuous addition of methanol, and trace elements to culture media together controlling pH, with continuous addition of pure oxygen.

In a preferred version, a wild type strain such as MGA3 is grown in a 14 liter fed batch fermentor in MV media. Methanol is fed continually to maintain a dissolved methanol concentration of about 100 mM. The pH of the culture is maintained at about 6.5–7, and dissolved oxygen at about 10% to about 45% air saturation. The strain of bacteria is typically grown for 16–30 hours. Glutamate is overproduced and excreted into the media at a concentration of at least about 20–30 g/l.

While not in any way meant to limit the invention, it is believed that deregulation of certain key enzymes in the biosynthetic pathways shown in FIG. 6, provides for overproduction of amino acids, such as glutamate.

If desired, the glutamic acid produced in the culture can be separated using known extraction procedures such as ion exchange chromatography. In a preferred method the fermentation broth including the *Bacillus methanolicus* strain, culture media components and amino acids produced is dried directly to produce a material containing cells, media components and one or more over produced essential amino acids which are useful as an animal feed or animal feed supplement. The fermentation broth can be dried by, for example, the method reported in G. L. Solomons, *Materials and Methods in Fermentation*, (Academic Press, N.Y. 1964).

The present invention may be better understood with reference to the following examples. These examples are intended to be representative of specific embodiments of the invention, and are not intended as limiting the scope of the invention.

EXAMPLE 1

Isolation and Characterization of *Bacillus methanolicus* Strain MGA3

A. METHODS AND PROCEDURES

Growth and Sporulation Media: Minimal salts medium (MS) contained in one liter of distilled water: $K_2HPO_4$, 3.8 g; $NaH_2PO_4.H_2O$, 2.8 g; $(NH_4)_2SO_4$, 3.6 g; $MgSO_4.7H_2O$, 0.5 g; $FeSO_4.7H_2O$, 2 mg; $CuSO_4.5H_2O$, 40 µg; $H_3BO_3$; 30 µg; $MnSO_4.4H_2O$, 200 µg; $ZnSO_4.7H_2O$, 200 µg; $Na_2MoO_4$, 40 µg; $CaCl_2.2H_2O$, 5.3 µg; $CoCl_2.6H_2O$, 40 µg. The pH of this medium was adjusted to 7.0 prior to autoclaving. The phosphates were reduced by 50% when MS medium was used for continuous cultures.

The minimal vitamin medium (MV) was MS medium supplemented with thiamine-HCl, D-calcium pantothenate, riboflavin, and nicotinamide, each at 50 µg/l, biotin and folic acid, each at 20 µg/l and $B_{12}$ at 1 µg/l.

Yeast extract medium (MY) was MS medium supplemented with yeast extract 0.5 g/l.

All media (MV and MY) contained 0.4% (vol/vol) methanol unless otherwise stated. Nutrient broth (NB) contained beef extract 3 g and peptone 5 g in 1000 ml distilled water. J vitamin medium (JV) contained tryptone (5 g) and yeast extract (15 g) per liter and the vitamins at the same concentration as MV medium. Sporulation medium (SM) was composed of three parts NB and four parts MV medium. All solid media was prepared by combining double strength medium components with an equal amount of 3% bacto agar after autoclaving.

Enrichment: Freshwater marsh soil was suspended in distilled water and heated for 20 minutes at 90° C. A portion of this suspension was used as an inoculum for the fermentors operating as batch cultures at 53° C. When growth was apparent in the vessels, the medium pumps were turned on and the flow rate was gradually increased to produce continuous cultures for enrichment.

Continuous Cultures: Two 1-liter Omni-Culture fermentors (The Virtis Company, Gardiner, N.Y.) were used for continuous cultures. A metering pump (Ismatec Mini, Chicago, Ill., S-820) fed an unsterilized MS medium into the vessels and flow was adjusted between 0.1 and 0.5 volumes per hour. A separate metering pump fed methanol at a rate that maintained a residual concentration of approximately 2 g/l in the out-flow. The concentration of methanol was measured by gas chromatography. The pH was automatically controlled at pH 6.8 by the addition of 10% v/v ammonium hydroxide (Controller Model 5656-00, Cole Parmer Instrument Co., Chicago, Ill.). The temperature was maintained between 53° C. and 56° C. Air was sparged at 2 v/v/m and three flat blade turbine impellers were operated at 600 RPM.

Isolation of Pure Cultures: Samples from the fermentors were periodically streaked on MY and MV agar and incubated at 53° C. Isolated colonies that were obtained from these plates were restreaked and grown under the same conditions. Colonies were tested for growth on methanol by inoculating 2 ml of MV medium into 18 mm tubes and incubating the tubes in a gyratory water bath shaker at 53° C. Tubes with growth in this methanol minimal broth were streaked onto MV agar for further purification.

Morphological Characteristics: Gram strain, spore strain, and poly-b-hydroxy-butyrate straining were done as described in the Doetsch, *Manual of Methods for General Bacteriology* at pp. 21–33 (American Society for Microbiology, 1981). Gram strains were verified with the KOH test conducted as described by Gergersen, supra. Cell size was determined with cells grown on MY agar for 18 hours at 50° C.

Characterization Tests: The API Rapid CH and Rapid E strip systems (Sherwood Medical, Plainview, N.Y.) were used to provide a standardized fermentation study of 49 substances and nine additional biochemical determinations respectively. Cultures used to inoculate two sets of strips were grown for 18 hours at 55° C. on the JV agar medium and on SM agar medium. The test strips were inoculated and read according to the directions provided with the system. Tests for nitrate reduction, NaCl tolerance, tyrosine decomposition, and lysozyme tolerance were performed as described by Gordon et al., *The Genus Bacillus Handbook No. 427* (Washington, D.C., Dept. of Ag. (1973)), but with the following changes. The reduction of nitrate to nitrite, NaCl tolerance, and lysozyme tolerance were tested in JV medium; tyrosine decomposition was tested in JV medium with tyrosine (5 g/l) and 0.5% methanol. To test the suitability of nitrate as an nitrogen source, potassium nitrate (5 g/l) was substituted for the ammonium sulfate in the MV medium.

Hydrolytic Activity: MV agar plates with 0.5% (vol/vol) methanol, were prepared to detect hydrolytic activity by adding soluble starch (3 g/l), fruit pectin (Certo Brand, 10 g/l), and gelatin (Sigma Type I, 4 g/l) to MV media prior to pouring the plates. Plates containing casein were prepared with 15 g non-fat dry milk (Carnation Company) in a liter of half-strength MV media. Hydrolysis on these plates was detected as described in Laskin and Lechevalier, *CRC Handbook of Microbiology*, pp. 734–735 (CRC Press, 1971).

Dipicolinic Acid Extraction and Determination: Dipicolinic acid (DPA) was extracted by autoclaving 5 ml samples of cell suspensions for 20 minutes. The samples were then cooled, acidified with 1 ml of 1N acetic acid, allowed to stand for 1 hour, and then centrifuged at 12,000×g for 10 minutes. The amounts of DPA in the supernatant fractions were determined by the colorimetric assay described by Janssen et al. *Science*, 127:26–27 (1958). Sporangia and cell counts were determined visually with the use of a Petroff-Hauser counting chamber.

Heat and chloroform resistance: A portion of culture was heated to 80° C. and then maintained at 80° C. for 10 minutes. Viable and heat stable counts were determined by plating appropriate dilutions of the heated and unheated culture on MY agar. The plates were incubated at 45° C. for 48 hours before the colonies were counted. A spore suspension was prepared from a culture grown at 50° C. for 18 hours and at 37° C. for 18 hours in MY. The culture was centrifuged at 12,000 g, washed, in distilled water by centrifugation and resuspended in distilled water. The spore suspension was pasteurized at 65° C. for 10 minutes. A portion of this suspension was then heated at 80° C. for 10 minutes. Spore counts were determined by plating dilutions on MV agar and incubating the plates at 50° C. for 48 hours.

Chloroform, 5 μl, was added to test tubes (13 mm×100 mm) containing 1 ml of a culture. After mixing the suspension on a vortex mixer, the tube was incubated at 37° C. for 10 minutes prior to dilution and plating as described above.

Growth Experiments: The growth responses to various substrates were determined in MV medium containing alcohols, at 0.5% (vol/vol); sugars, organic acids and methyl substituted amines, each at 0.3% (wt/vol); and formaldehyde, at 0.03w (wt/vol). The effects of pH on growth were determined in MV medium with the pH adjusted by addition of HCl or NaOH. Growth rates were determined by growth of culture in triple baffled flasks (Bellco Model 2540) on a gyratory shaker (New Brunswick Model G-7) operated at approximately 200 RPM. Growth was measured by turbidimetric measurements at 650 nm using a spectrophotometer or Klett units (#66 filter), using a Klett Summerson calorimeter. One absorbance unit was equivalent to 0.42 g/l of dry cell weight.

Antibiotic Susceptibility: An 0.2 ml volume of a mid-exponential phase culture was spread onto MV agar plates containing 0.5% vol/vol methanol. The plates were incubated for 1 hour at 55° C. to dry the surface. Antibiotic containing discs (Difco Laboratories, Detroit, Mich.) were then aseptically placed on the surface and the plates were returned to 55° C. for 48 hours. The antibiotic discs used to test susceptibility contained gentamicin 10 mcg, sulfadiazine 300 mcg, tetracycline 30 mcg, ampicillin 10 mcg, rifampin 5 mcg, chloromycetin 30 mcg, erythromycin 5 mcg, and penicillin G 10 units.

Methanol Oxidation: Cultures of Bacillus strain MGA3 were grown to mid-exponential phase in liquid MV media with methanol (4 g/l) or mannitol (3 g/l) at 50° C. Cells were harvested at 40° C. by centrifugation at 12,000×g for 8 minutes, washed by centrifugation in ice cold 0.05 M phosphate buffer pH 7.0 and suspended in ice cold 0.05 M phosphate buffer. Methanol oxidation was measured using a Rauk oxygen electrode (Rauk Bros., Bottisham, England). Oxygen consumption was measured by placing a suspension of cells (3.7–7.3 mg/mL) in 0.05 M phosphate buffer in the electrode. After the rate of endogenous oxygen consumption was established, methanol 1.0 g/l was added to the electrode and the rate of methanol dependent oxygen consumption was measured.

Crude Extracts and Enzyme Assays: Cells were harvested in mid-exponential phase, resuspended in 50 mM phosphate buffer, pH and disrupted by two passages through a French pressure cell operated at 15,000 psi. The cell debris was separated by centrifugation at 12,100 g and the supernatant fraction was used as the crude extract. Hexulose phosphate synthase was assayed by the method of Cox and Zatmann, *J. Biochem*, 141:605–608 (1974), incorporated by reference herein; and hydroxypyruvate reductase was assayed by the method of Large and Quayle, *J. Biochem*, 87:387 (1963), incorporated by reference herein. Protein concentrations were determined with Biuret reagent by the method of Clark and Switzer, *Experimental Biochemistry* (2nd ed., Freeman Press, 1977), incorporated by reference herein. Bovine serum albumin was employed as a standard.

DNA Base Composition: The DNA base composition was determined by measuring the hyperchromic shift in absorbance as a function of temperature in 0.12 M sodium phosphate pH 6.8 with *E. coli* DNA as a standard, Mandel and Marmur, *Methods Enzymol.*, 1:195–206 (1968).

B. RESULTS

Enrichment and Isolation: Development of a methanol-utilizing mixed culture at 53–56° C. was rapid and abundant. When a continuous culture was established, dilution rates could be raised to 0.45 per hour without washout. Smears revealed a preponderance of Gram positive forms including spore-forming bacteria, and a variety of morphological types including some very large pleomorphic cells. However, only bacteria that did not grow when returned to methanol minimal medium could be readily isolated from the enrichment vessels. After screening many isolates, (using the isolation procedure described above one was found that grew rapidly in MV medium at 53° C. and was given the strain designation MGA3.

Cell and Colony Morphology: Cells of strain MGA3 were rod shaped (0.8–1.0 by 2.5–4.5 μm) with rounded ends (FIG. 1). Young cultures stained Gram positive and all cultures were KOH negative. V-shaped pairs of cells were frequent in cultures. Vacuoles were never seen and poly-b-hydroxybutyrate was not detected by Sudan black B staining. Colonies produced on MV agar were colorless, translucent, circular, convex, and had entire margins. Streak cultivation produced colonies of various sizes and all colonies grew larger on MV agar supplemented with amino acids, glucose, yeast extract, or small amounts of nutrient broth than on unsupplemented MV agar. Pigments were not produced.

Figure 3:
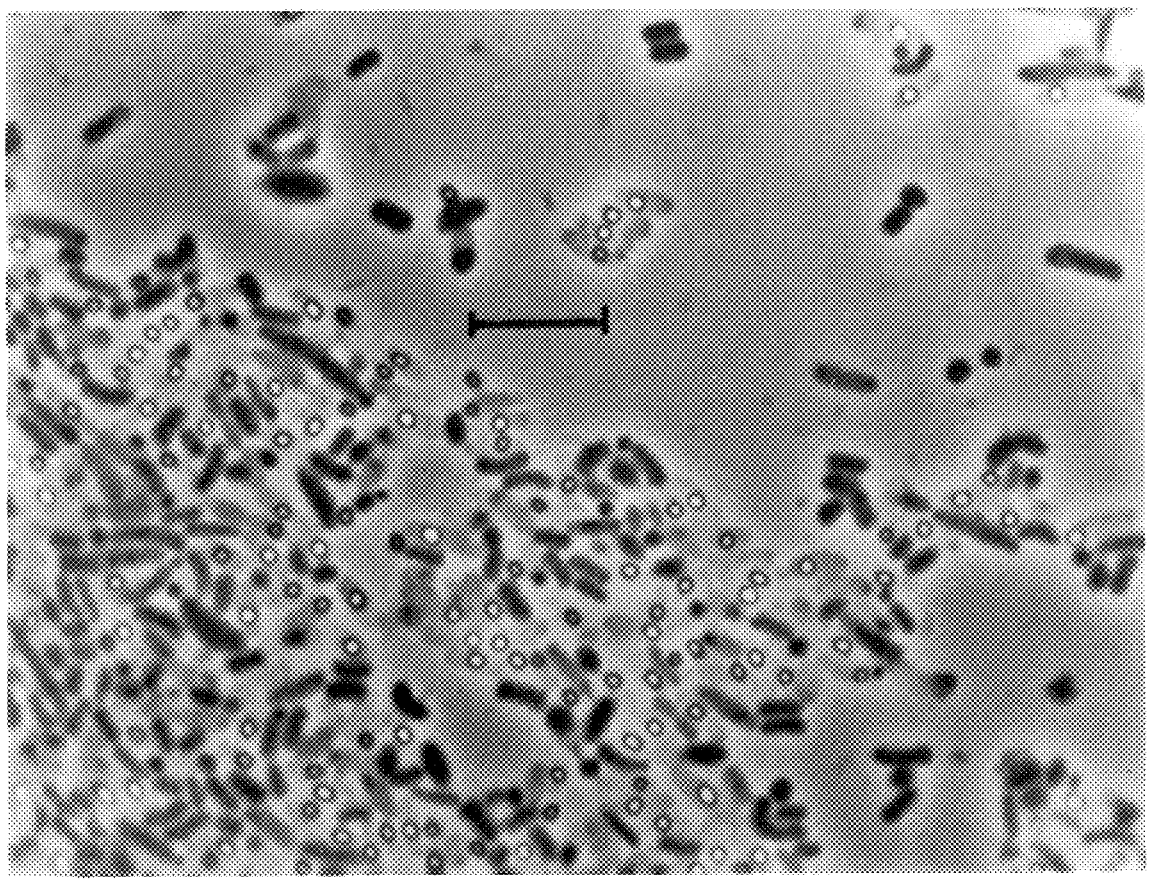
FIG. 3 is a phase contrast photomicrograph of strain MGA3 grown on SM medium at 53° C. and shifted to 37° C. The bar represents 10 μm.

Endospores: Spores were oval and 0.8–1.0 by 1.1–1.2 μm, their location was subterminal and sporangia were swollen (FIG. 3). It was noticed that most cultures grown on MV agar at 53° C. did not contain refractile endospores and lost viability rapidly when stored at room temperature. These cultures did not grow when inoculated into fresh media. However, cultures that contained endospores produced growth in fresh media even after heating at 80° C. for 10 minutes. Strain MGA3 grew well at 50–55° C. but most cells lysed without producing endospores. It was noted that endospores were formed in cultures that were incubated at 50–55° C. for 18 hours and then incubated at 37° C. for an additional 18 hours. When cultures were grown under these conditions 54% of the cells contained refractile endospores and chloroform resistant colony forming units were equal to 10% of the viable cell counts ($2.7 \times 10^{-7}$ viable cells×$ml^{-1}$). It was also noted that supplemented methanol media (MY, SM) produced more endospores than the minimal medium (MV). Nutrient agar or nutrient agar with added manganese sulfate (5 mg.$l^{-1}$) did not serve as a good sporulation media.

Heat Tolerance: Exponential-phase cultures of MGA3 grown at 50° C. and containing $3.1 \times 10^8$ colony forming units (CFU) per ml were completely killed by heating for 10 minutes at 80° C. A pasteurized spore suspension from cultures grown 18 hours at 53° C. and incubated an additional 18 hours at 37° C. contained $7.37 \times 10^7$ CFU when plated on a methanol-salts medium (MV). The same suspension contained $3.5 \times 10^7$ CFU after heating at 80° C. for 10 minutes.

Dipicolinic Acid: Dipicolinic acid is a compound absent from vegetative bacteria but present in large amounts in endospores. A culture of *Methylophilus methylotrophus* grown in MV medium at 37° C. and a culture of strain MGA3 grown in MV at 50° C. and then switched to 37° C. were each the source of 70 mg (wet weight) of cell paste. Each cell paste was extracted and assayed for dipicolinic acid. The cells of *Methylophilus methylotrophus* contained no detectable dipicolinic acid while the cells of MGA3 contained 0.189 mg dipicolinic acid.

Growth: Strain MGA3 grew well in J medium, a complex medium used to grow fastidious species of Bacillus, Gregersen, *Eur. J. Appl. Microbiol. Biotechnol.*, 5:123–123 (1978) incorporated by reference herein, and grew poorly in nutrient broth or on nutrient agar. The organism grew rapidly in MV medium that contained methanol or mannitol. Of the vitamins present in this medium, only vitamin $B_{12}$ stimulated growth and both vitamins $B_{12}$ and biotin was absolutely required for growth. Strain MGA3 grew more slowly when the medium contained glucose as the source of carbon and energy. Maltose, ribose, acetate, glutamate, and alpha-ketoglutarate were utilized poorly, and growth from galactose was scant or doubtful. Lactose, sucrose, xylose, formate, succinate, glycerol, ethanol, n-propanol, n-butanol, formaldehyde, methylamine, diethylamine, or trimethylamine were not utilized.

Acid was produced from only 7 of the 49 substrates used in the API rapid CH test (ribose, D-glucose, mannitol, maltose, D-tagatose, D-arabitol, and 5-keto-gluconate). Gas was not produced from any of the following substrates: Glycerol, erythritol, D-arabinose, L-arabinose, D-xylose, L-xylose, adonitol, beta-methyl-xyloside, galactose, D-fructose, D-mannose, L-sorbose, rhamnose, dulcitol, inositol, sorbitol, alpha-methyl-D-mannoside, alpha-methyl-D-gluconate, N-acetyl-glucosamine, amygdalin, arbutin, esculin, salicin, cellobiose, lactose, melibiose, saccharose, trehalose, insulin, melezitose, D-raffinose, starch, glycogen, xylitol, b-gentiobiose, D-turanose, D-lyxose, D-fucose, L-fucose, L-arabitol, gluconate, or 2-keto-gluconate.

Strain MGA3 grew in JV broth that contained 1% NaCl but not in broth that contained 5% NaCl.

Growth on Methanol: Of the eight vitamin components in MV medium, only vitamins $B_{12}$ and biotin was required for growth of strain MGA3 on methanol. If vitamin $B_{12}$ is eliminated from MV medium, growth of strain MGA3 does not occur. Nitrate was not utilized as a nitrogen source.

Growth of strain MGA3 in methanol was optimal at pH 7.0–7.5. Growth did not occur at pH 5.5. The optimum growth temperature was found to be between 50 and 53° C. The organism grew in MY medium at 30 and at 61° C.; it failed to grow at 25 and 65° C.

TABLE II

The effect of temperature on the growth rate of Bacillus Strain MGA3 in medium MV.

| Temperature Degree | $\mu$ ($h^{-1}$) |
|---|---|
| 37 | 0.24 |
| 45 | 0.41 |
| 50 | 0.51 |
| 53 | 0.43 |
| 56 | 0.38 |

Figure 4:
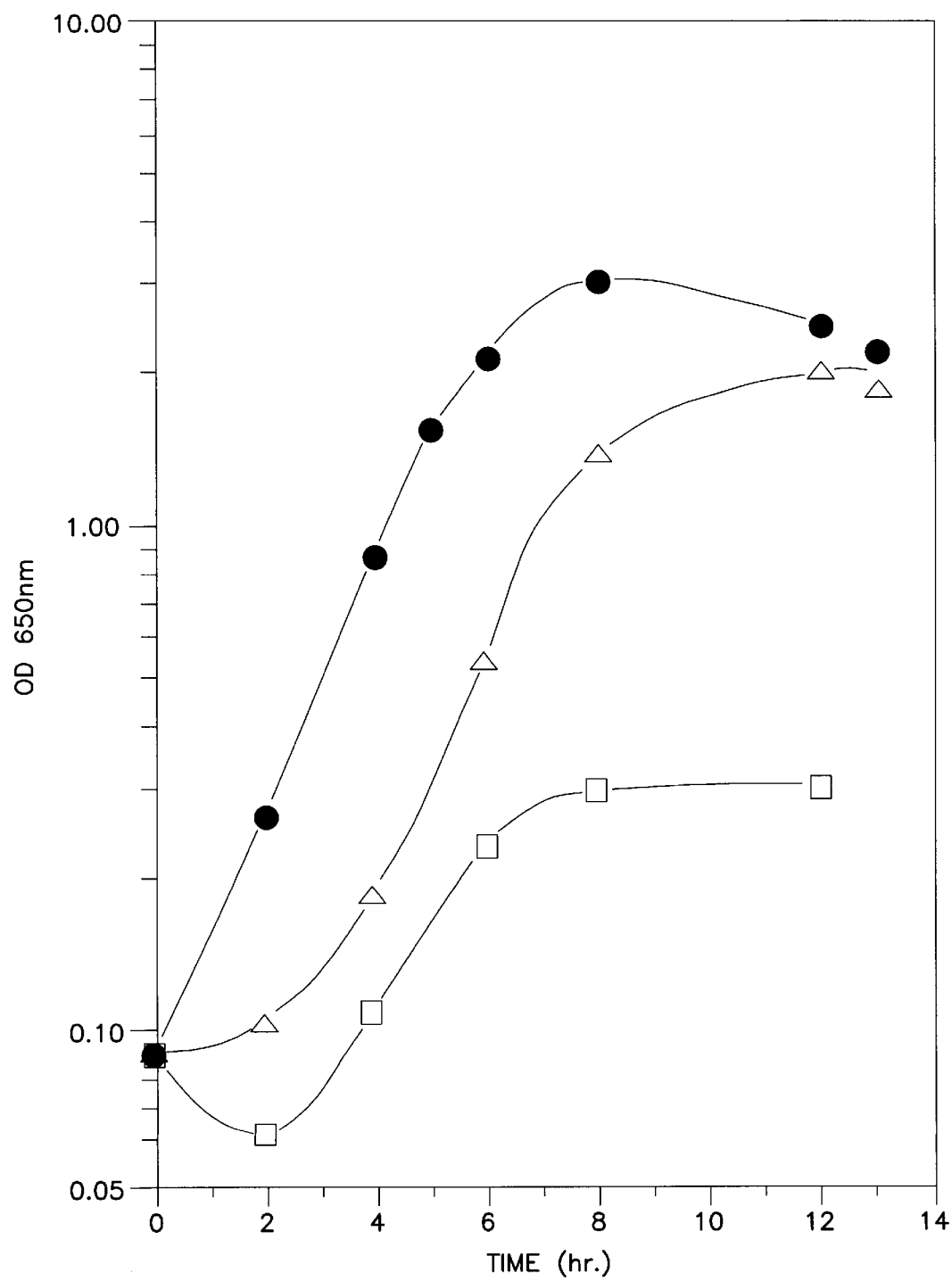
FIG. 4 shows growth of *Bacillus methanolicus* strain MGA3. Strain MGA3 was inoculated into MV media containing 0.5 g/l yeast extract (-o-), methanol 5.0 g/l (-Δ-), or methanol 5 g/l and 0.5 g/l yeast extract (-··-). The cultures were incubated with shaking at 53° C.
Figure 5:
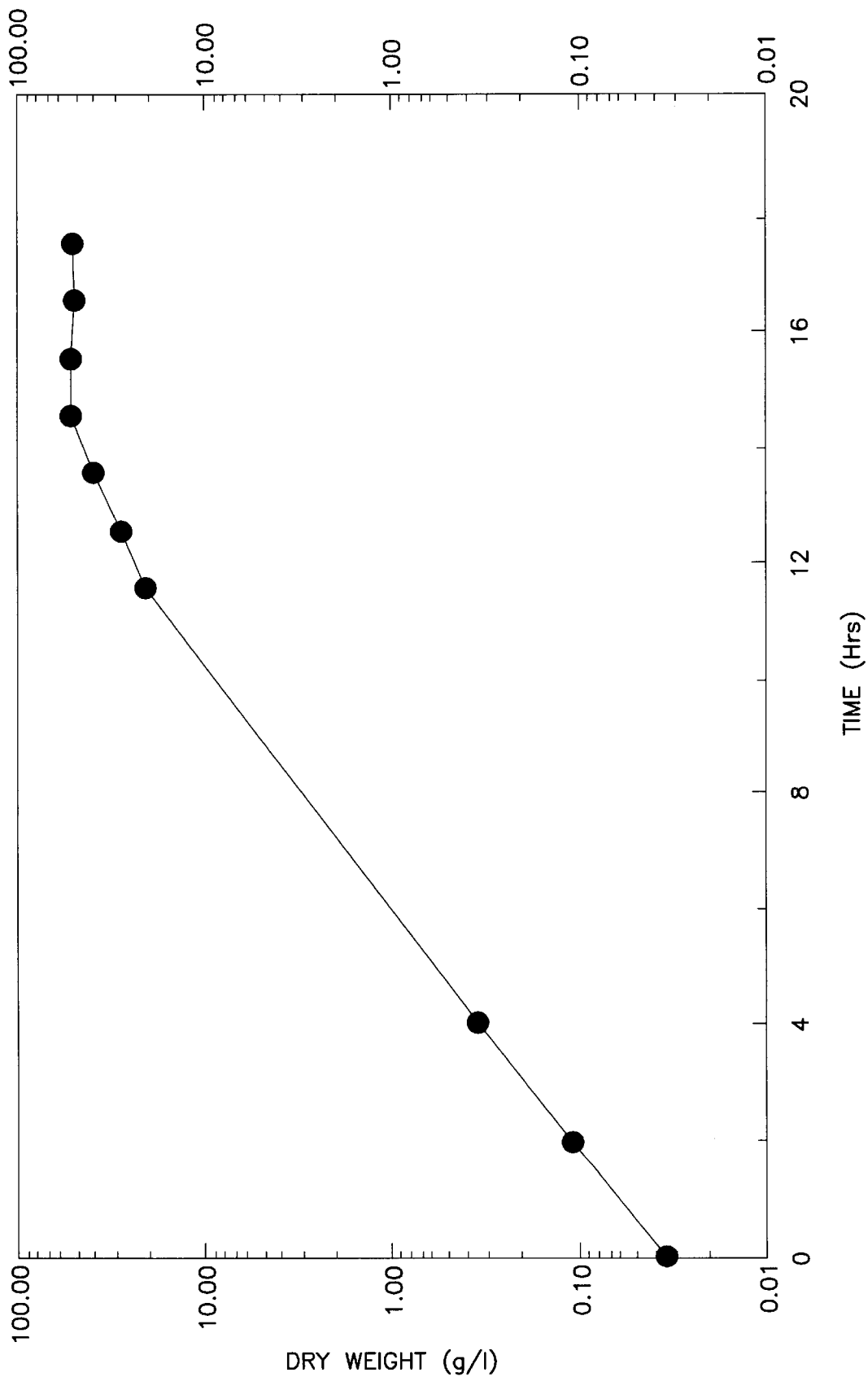
FIG. 5 shows MGA3 growth to high cell density under semi-continuous or fed-batch conditions.

Strain MGA3 had a generation time of 1.4 hours in MV medium at 50° C. Growth on methanol was stimulated by the small additions of complex nutrient mixtures such as yeast extract. Generation times were reduced to approximately 1 hour in these media (FIG. 4).

Biochemical Characterization: Crude cell extracts prepared from methanol grown cultures of MGA3 lacked hydroxypyruvate reductase activity but contained high hexulose-6-phosphate synthase activity. The specific activity of hexulose-6-phosphate synthase was 6.27–3.72 μm of formaldehyde utilized per minute per mg of protein. Strain MGA3 did not produce catalase or tyrosine-degrading enzymes. Starch, gelatin, and pectin were hydrolyzed but growth was inhibited on casein containing plates. The API Rapid E tests indicated the presence of cytochrome oxidase, urease and acetoin. The Rapid E tests for b-galactosidase, lysine decarboxylase, ornithine decarboxylase, citrate utilization, phenylalanine deamination, and indole were negative. Nitrate was not reduced to nitrite.

Methanol oxidation by cell suspensions grown with methanol or mannitol as carbon and energy sources was measured at 50° C. and 37° C. Cells grown with methanol as the carbon and energy source oxidized methanol at a rate of $5.8 \times 104$ mmoles.$min^{-1} \times mg^{-1}$ at 37° C. Cells grown with mannitol as the carbon and energy source oxidized methanol at a rate of $6.5 \times 10^{-5}$ mMoles.min×$mg^{-1}$ at 50° C.

Antibiotic Susceptibility: Strain MGA3 was sensitive to all antibiotics tested.

DNA Base Composition: DNA isolated from strain MGA3 had a base content of 44 moles per cent G+C.

A comparison of the identifying characteristics of Bacillus strain MGA3 with those described for strains of *Bacillus methanolicus* in Arfman et al., cited supra., indicates that Bacillus MGA3 can be classified as a strain of *Bacillus methanolicus*.

EXAMPLE 2

Glutamic Acid Determination

Glutamic acid was determined by HPLC using pre-column derivatization with o-phtalaldehyde (OPA) and fluorescence detection of the OPA-amino acid derivative. Culture supernatants were diluted 50–1000 fold with methanol, and then centrifuged for 2–5 minutes at high speed to remove any precipitated protein. The sample (25 µL) was then mixed with o-phtalaldehyde (Pierce #26015) (50 µL), then injected onto a 5µ particle size C-18 reverse phase column (Alltech #28066). Separation of the OPA amino acids was carried out using a flow rate of 1 mL/min and a non-linear gradient from 10–50% methanol in 50 mM potassium phosphate (pH 6.8).

EXAMPLE 3

Glutamic Acid Production by Wild type *Bacillus methanolicus* in Shake Flasks For screening of potential glutamic acid producers, wild type strains, including MGA3, were grown on medium containing in one liter of distilled water: $K_2HPO_4$, 5.1 g; $NaH_2PO_4.H_2O$, 1.9 g; $(NH_4)_2SO_4$, 3.6 g; $MgSO_4.7H_2O$, 0.25 g; $FeSO_4.7H_2O$, 4 mg; $CuSO_4.5H_2O$, 28 µg; $CaCl_2.2H_2O$, 7.4 mg; $CoCl_2.6H_2O$, 40 µg; $MnCl_2.4H_2O$, 9.9 mg; $ZnCl_2$, 136 µg; $Na_2MoO_4$, 48 µg; $H_3BO_3$; 30 µg. The media also included biotin, 200 mg/L and vitamin B12, 1 mg/L. MGA3 was grown in 250 mL non-baffled shake flasks containing 100 mL of the media described above plus a carbon source. Several carbon sources were tried in efforts to induce the greatest production of glutamate from wild type strains in shake flasks. The carbon sources were: 2% methanol, 1.6% methanol plus 40 mM sodium acetate, and 1.5% mannitol. The concentrations refer to concentrations in the shake flasks.

The cultures were started using a 1–4 inoculum and grown at 50° C. and rotated at 400 rpm. The concentration of methanol was determined every 12 hours by removing a sample, separating the cells by centrifugation, and injecting the supernatant into a gas chromatograph. More methanol was added to the flask if the concentration dropped below 200 mM. Experiments were usually carried out for a period of 24–48 hours.

The amount of glutamate produced determined by HPLC of the OPA derivative amino acids. The amount of glutamate formed varied with the carbon source, but was always quite low, <0.5 g/L (Table III). Mannitol as a carbon source resulted in the greatest amount of glutamate observed in shake flasks experiments. When yeast extract was added to the media at 0.05%, the level of glutamate formed dropped below background levels for detection.

TABLE III

Glutamate Produced by MGA3 in Shake Flasks

| Carbon Source | Glutamate |
| --- | --- |
| Methanol (2%) | 27 mg/L |
| Methanol (1.6%) plus Sodium Acetate 40 mM | 43 mg/L |
| Mannitol (1.52%) | 101 mg/L |

Previously known glutamate producing wild type strains require sub-optimal levels of biotin, sub-lethal doses of penicillin, or the use of surfactants to achieve high levels of glutamate production. Limiting concentrations of biotin in cultures of MGA3 in shake flasks was evaluated, and no significant increase in glutamate production was observed. The surfactants Span 20, Tween 40, and Tween 60 were also examined and found to have no significant impact on the amount of glutamate produced in shake flask cultures of MGA3. It was not possible to attain sub-lethal doses of penicillin in shake flasks, so the effect of penicillin on glutamate production could not be determined in shake flasks.

These results with cultures of MGA3 in shake flasks indicate that the wild type strain MGA3 fails to produce significant levels of glutamate.

EXAMPLE 4

Glutamic Acid Overproduction by Wild type *Bacillus methanolicus* in a Stirred Reactor Generally in a stirred reactor cells can be cultured with growth rates from 0.5–1 µmax using the following concentration ranges of nutrients.: ammonium sulfate from 20–500 mM, sulfate from 0.1–500 mM, methanol from 20–800 mM, phosphate from 10–125 mM, magnesium from 0.5–20 mM, manganese from 2–100 mM, iron from 10–800 mM, calcium from 0.1–1.5 mM, chloride from 0–80 mM, zinc from 1–20 mM, cobalt from 0.1–20 mM, copper from 0.1–20 mM, molybdate from 0.2–40 mM, borate from 0.4–8 mM, vitamin $B_{12}$ from 0.5 mg/l–1 mg/l, and biotin from 6 µg/1–20 mg/l.

Glutamic acid was over produced in the aerated stirred reactor by culturing the appropriate wild type strain, such as MGA3, under defined conditions. Growth of MGA3, or another wild type strain, in the bioreactor requires control of methanol levels, dissolved oxygen levels, pH, and temperature. All experiments were carried out at 50° C. with methanol levels controlled at 100 mM, dissolved oxygen levels maintained by supplementation of the air sparge with pure oxygen, and pH controlled by the addition of either anhydrous ammonia or 30% ammonium hydroxide.

The reactor was batched with phosphate salts, yeast extract, ammonium sulfate, and biotin in a medium including in each liter: $K_2HPO_4$, 4.1 g; $NaH_2PO_4.H_2O$, 1.5 g; $(NH_4)_2SO_4$, 2.1 g; yeast extract, 0.25 g; biotin, 0.6 mg; and antifoam SAG-471, 0.5 mL. After sterilization, trace metals, methanol, and vitamin $B_{12}$ are added so the media included the following ingredients in each liter of media: $MgSO_4.7H_2O$, 0.25 g; vitamin $B_{12}$, 10 µg; $FeCl_2.4H_2O$, 7.9 mg; $CuCl_2.2H_2O$, 15 µg; $CaCl_2.2H_2O$, 15 mg; $CoCl_2.6H_2O$, 81 µg; $MnCl_2.4H_2O$, 20 mg; $ZnCl_2$, 273 µg; $Na_2MoO_4$, 97 µg; $H_3BO_3$; 61 µg and 100 mM methanol.

The methanol feed typically contained trace metals in each liter of methanol at levels of about: $MgCl_2.6H_2O$, 3.5 g; $FeCl_2.4H_2O$, 0.78 g; $MnCl_2.4H_2O$, 0.5 g; $CuCl_2.2H_2O$, 13 mg; $CoCl_2.6H_2O$, 19 mg; $Na_2MoO_4.2H_2O$ 22 mg; $ZnCl_2$, 22 mg. A methanol feed including only low concentrations of metals was also used in certain experiments. The low metal methanol feed included in each liter of methanol: $MgCl_2.6H_2O$, 3.5 g; $FeCl_2.4H_2O$, 0.065 g; $MnCl_2.4H_2O$, 0.16 g; $CuCl_2.2H_2O$, 1 mg; $CoCl_2.6H_2O$, 1 mg; $Na_2MoO_4.2H_2O$ 1 mg; $ZnCl_2$, 2 mg; $CaCl_2.2H_2O$, 121 mg; $H_3BO_3$, 1 mg. Trace metals are fed with the methanol by adding a concentrated solution of the metals to the methanol.

All reactor runs were carried out in a 20 L Biolafitte, 7 L NBS, or 14 L Chemap reactor equipped with the controls described above. It is believed that the formation of glutamate from methanol by MGA3 depended on several factors including: cell dry weight (CDW), trace metals, dissolved oxygen, Tween 80, and pH, but not biotin or penicillin. Each of these are addressed below.

(1) Cell Dry Weight (CDW): In all fermentations, with non-limiting concentrations of magnesium, glutamate formation was insignificant (<5 g/L) until the cell density approaches 20 g/L. In a reactor run that made 3–4 g/L cell dry weight, only 200–300 mg/L of glutamate was formed. Fermentations that resulted in >20 g/L cell dry weight gave >13 g/L glutamate. The higher cell dry weight lead to improved levels of glutamate. As is shown below, high cell dry weight alone is not sufficient for glutamate formation, but appears to be required, when magnesium is present at non-limiting concentrations.

In the presence of limiting concentrations of magnesium, glutamate production was insignificant (<2 g/L) until the cell density approaches 10 g/L.

(2) Trace Metals: The levels and type of trace metals in the fermentation had large effects on the production of cells and glutamate. When cells were grown with the metals described above for the medium and the typical metal containing methanol feed, 28 g/L of cell dry weight and 31 g/L of glutamate were obtained.

However, when the cells were grown in the same medium except that copper, cobalt, and molybdenum were eliminated from the methanol feed, 23 g/L cell dry weight made only 3 g/L of glutamate. When copper was added back into the methanol feed, the cell dry weight returned to 28 g/L and the amount of glutamate produced was 30 g/L.

When the cells were grown the same medium except that magnesium ion was eliminated from the methanol feed, 14 g/L cell dry weight made 44 g/L of glutamate. In the presence of limiting magnesium ion, high levels of glutamate were produced at lower levels of cell dry weight.

Growth of cells using the low metal methanol feed described above resulted in 26 g/L of cell dry weight and only 14 g/L glutamate.

The data on these metals, summarized in Table IV, demonstrate that metals are a major factor in glutamate formation and that high cell dry weight alone is not sufficient for glutamate formation by MGA3.

TABLE IV

Metal Effects on Glutamate Formation

| CDW (g/L) | Glutamate (g/L) | Methanol Feed |
|---|---|---|
| 29 | 31 | Typical metals |
| 23 | 14 | Low metal |
| 23 | 3 | Typical metal feed lacking cobalt, copper, and molybdenum |
| 30 | 31 | Typical metal feed lacking cobalt and molybdenum |
| 11 | 4 | Typical metal feed lacking cobalt, molybdenum, and zinc |
| 33 | 23 | Typical metal feed lacking manganese |
| 43 | 29 | Typical metal feed lacking iron |
| 14 | 44 | Typical metal feed lacking magnesium |

(3) Dissolved Oxygen: Several runs were made at different levels of dissolved oxygen. In a run in which dissolved oxygen was allowed to fall to 0, the cell dry weight was 15 g/L, but only 0.26 g/L of glutamate was formed. With dissolved oxygen levels maintained at 30% of saturation by oxygen enrichment, the cell dry weight increased to 33 g/L, a 2.2-fold increase, and glutamate levels increased 135-fold to 35 g/L.

TABLE V

Effect of Dissolved Oxygen on Glutamate Formation

| CDW (g/L) | Glutamate (g/L) | Dissolved Oxygen Level (% saturation) |
|---|---|---|
| 31 | 33 | 45 |
| 33 | 35 | 30 |
| 39 | 32 | 15 |

(4) Surfactants: The effect of several surfactants on the level of glutamate produced by MGA3 from methanol was investigated in the reactors using the typical salts described above as batched into the reactor and added after sterilization and the typical concentrations of metals in the methanol feed. Unless stated otherwise, the reactor was batched with media and surfactant, then innoculum was added to the reactor. The results of these studies are shown in Table VI. At the concentration tested, Tween 80 gave the best results, 57 g/L glutamate and a 30carbon conversion from methanol to glutamate. When Tween 80 was used at 4 g/L, it was inhibitory, only 15 g/L of glutamate and 20 g/L cell dry weight were formed. In the CTAB run, the cells were grown to a density of 25 g/L, then the CTAB was added. The amount of CTAB used also differs from the other surfactants, only 2 mg/L were required to show improved glutamate production while the other surfactants have been tested at the level of 2 g/L.

TABLE VI

Effect of Surfactants on Glutamate Formation

A.

| CDW (g/L) | Glutamate (g/L) | Surfactant |
|---|---|---|
| 29 | 24 | None |
| 45 | 8.5 | Span 20 at 4 g/L |
| 43 | 25 | Tween 60 at 4 g/L |
| 37 | 29 | Tween 80 at 1 g/L |
| 28 | 57 | Tween 80 at 2 g/L |
| 20 | 15 | Tween 80 at 4 g/L |

B.

| Surfactant | Carbon Conversion (%) | CDW (g/L) | Glutamate (g/L) |
|---|---|---|---|
| None | 20 | 33 | 35 |
| 2 g/L Tween 60 | 20 | 37 | 35 |
| 4 g/L Tween 60 | 22 | 38 | 33 |
| 2 g/L Tween 40 | 19 | 44 | 39 |
| 2 mg/L CTAB | 25 | 35 | 54 |
| 2 g/L Span 20 | 9 | 1.75 | 1.95 |
| 2 g/L Tween 20 | 8 | 1.37 | 1.91 |
| 2 g/L Tween 61 | 7 | 27.1 | 27.4 |
| 2 g/L Tween 85 | 19 | 29.6 | 35.8 |

When Tween 80 was added (final conc. 2 g/L) to growing cultures of MGA3 under the standard coditions, little if any improvement in glutamate production was observed. This was true even when Tween 80 was added early or late during the growth phase of MGA3. These results are reported in Table VII, part A.

When MGA3 cells were inoculated into a reactor that had been batched with Tween 80 at 2 g/L, improved glutamate production was observed. This improvement correlated with higher inoculum density.

TABLE VII

Effect of Timing of Addition of Tween 80

A. Results when Tween 80 was added to a reactor containing growing B. methanolicus.

| CDW (g/L) | Glutamate (g/L) | Carbon Conversion | Condition |
|---|---|---|---|
| 33 | 35 | 20 | No Tween 80 |
| 30 | 37 | 20 | Tween added at OD500 0.5 |
| 30 | 41 | 28 | Tween 80 added at OD500 42 |
| 46 | 36 | 14 | Tween 80 added at OD500 107 |

B. Results when B. methanolicus was inoculated into a reactor containing Tween 80.

| CDW (g/L) | Glutamate (g/L) | Carbon Conversion (%) | Condition |
|---|---|---|---|
| 33 | 35 | 20 | No Tween 80 |
| 28 | 57 | 30 | OD500 64 of inoculum |
| 33 | 58 | 36 | OD500 90 of inoculum |

(5) pH: The effect of pH was tested at four different levels, 6.5, 6.8, 7.2, and 7.4. A run at pH 6.8 produced 28 g/L of cell dry weight and 30 g/L of glutamate. A run at pH 7.2 produced 25 g/L of cell dry weight but only 20 g/L of glutamate. The lower pH led to better glutamate formation, demonstrating an effect of pH on glutamate formation.

(6) Biotin: Several levels of biotin were tested from 6000 µg/L to 6 µg/L, and little difference in glutamate formation was detected except at the lowest level of biotin (Table VII). At 6 µg/L biotin, production of glutamate decreased somewhat. At 6 µg/L, biotin was the limiting nutrient since the cell mass decreased to 21 g/L from 28 g/L. These experiments demonstrate that glutamate production from MGA3 is not enhanced by biotin limitation as with other glutamate producing organisms such as Corynebacterium. In fact, formation of glutamate from methanol by MGA3 was inhibited by biotin limitation.

TABLE VIII

The Effect of Biotin on Glutamate Formation

| CDW (g/L) | Glutamate (g/L) | Biotin (µg/L) |
|---|---|---|
| 29 | 28 | 6000 |
| 28 | 31 | 600 |
| 28 | 23 | 60 |
| 21 | 21 | 6 |

(7) Penicillin: The addition of penicillin to a reactor of growing MGA3 failed to enhance the amount of glutamate formed (Table IX). The sensitivity of MGA3 to penicillin made these experiments very difficult to do, and cell lysis was observed at all levels of penicillin tested. Although other wild type microbes show enhanced production of glutamate when cultured with penicillin, penicillin inhibited production of glutamate by MGA3.

TABLE IX

Effect of Penicillin on Glutamate Formation

| CDW (g/L) | Glutamate (g/L) | Penicillin (mg/L) |
|---|---|---|
| 29 | 28 | None |
| 23 | 17 | 1.0 |
| 17 | 16 | 1.0 |

(8) Phosphate, Asparagine and Isovalerate: Levels of phosphate, asparagine and isovalerate were varied independently.

When phosphate was limiting, the cell dry weight was 34 g/L and glutamate production was only 8 g/L. When phosphate was present in non-limiting amounts, cell dry weight rose only slightly to 35 g/L, but glutamate rose nearly 4-fold to 30 g/L.

Asparagine inhibited glutamate synthesis. A control run produced 22 g/L of cell dry weight and 33 g/L of glutamate. Addition of asparagine at 1 g/L/hr increased production of cells to 27 g/L cell dry weight, but decreased glutamate formation to the level of 16.5 g/L.

Isovalerate inhibited glutamate synthesis. A control run produced 28 g/L cell dry weight and 24 g/L glutamate. Isovalerate at 0.25 g/L had little effect on cell dry weight, 26 g/L produced, but caused marked inhibition of glutamate production, only 12 g/L were produced.

(9) Inoculum Density: Inoculum density was varied in the presence of Tween 80™ at 2 g/L. Increased inoculum density increased glutamate production while decreasing the cell dry weight (Table IX).

TABLE X

Effect of Inoculum Density on Glutamate Formation and Percent Carbon Conversion

| CDW (g/L) | Glutamate (g/L) | % Carbon Conversion | Inoculum Density (OD500) |
|---|---|---|---|
| 43 | 37 | 20 | 0.5 |
| 44 | 47 | 20 | 60 |
| 28 | 57 | 30 | 64 |
| 33 | 58 | 36 | 90 |

The data in the table shows that increased cell density decreases the cell dry weight while increasing the amount of glutamate produced. Increased inoculum density also increases the % carbon conversion. In this experiment, maximum glutamate production was achieved at inoculum densities of about 60 (OD500) to about 90 (OD500).

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

What is claimed is:

1. A method for producing glutamic acid, the method comprising the steps of:
   culturing a biologically pure culture of a non-auxotrophic *Bacillus methanolicus* isolated from a natural source in nutrient medium comprising methanol as the primary carbon source, a copper ion, and biotin at a cell density of more than about 20 g/L cell dry weight at a temperature of about 45° C. to about 60° C. until glutamic acid is produced and excreted at a concentration of at least about 20 g/L; and recovering the excreted glutamic acid from the nutrient media.

2. A method according to claim 1, wherein the *Bacillus methanolicus* comprises *Bacillus methanolicus* MGA3 (ATCC Deposit Designation 53907), *Bacillus methanolicus* NOA2 (ATCC Deposit Designation PTA-166), or a combination thereof.

3. A method according to claim 1, wherein the copper ion is provided as $CuCl_2$ or $CuSO_4$.

4. A method according to claim 1, wherein the copper ion is at more than about 1 mg/L.

5. A method according to claim 1, wherein the biotin is at more than about 60 μg/L.

6. A method according to claim 1, wherein the cell density is about 30 g/L cell dry weight.

7. A method according to claim 1, wherein the temperature is about 50° C.

8. A method according to claim 1, wherein glutamic acid is produced at a concentration of at least about 40 g/L.

9. A method according to claim 1, wherein glutamic acid is produced with a carbon conversion of methanol to glutamate of at least about 20%.

10. A method according to claim 9, wherein the carbon conversion is about 30%.

11. A method according to claim 1, wherein in the step of culturing, the oxygen level is maintained at about 10% to about 45% saturation.

12. A method according to claim 1, wherein the in the step of culturing, the pH is maintained at about 6.3 to about 7.

13. A method for producing glutamic acid, the method comprising the steps of:

culturing a biologically pure culture of a non-auxotrophic *Bacillus methanolicus* isolated from a natural source in nutrient medium comprising methanol as the primary carbon source, a copper ion, a surfactant, and a greater than limiting amount of biotin at a cell density of more than about 20 g/L cell dry weight at a temperature of about 45° C. to about 60° C. wherein glutamic acid is produced and excreted with a carbon conversion of methanol to glutamic acid of at least about 20%; and recovering the excreted glutamic acid from the nutrient media.

14. A method according to claim 13, wherein the surfactant is polyoxyethylene sorbitan monooleate or cetyltrimethyl ammonium bromide.

15. A method according to claim 14, wherein the surfactant is at about 2 g/L.

16. A method for producing glutamic acid, the method comprising the steps of:

culturing a biologically pure culture of a non-auxotrophic *Bacillus methanolicus* isolated from a natural source in nutrient medium comprising methanol as the primary carbon source and a limiting amount of magnesium ion at a temperature of about 45° C. to about 60° C. until glutamic acid is produced and excreted at a concentration of at least about 20 g/L; and recovering the excreted glutamic acid from the nutrient media.

17. A method according to claim 16, wherein the *Bacillus methanolicus* comprises *Bacillus methanolicus* MGA3 (ATCC Deposit Designation 53907), *Bacillus methanolicus* NOA2 (ATCC Deposit Designation PTA-166), or a combination thereof.

18. A method according to claim 16, wherein the magnesium ion is at less than about 1 mg/L.

19. A method according to claim 16, wherein the nutrient medium is substantially free of magnesium ion.

20. A method according to claim 16, wherein the cell are grown to a cell density of about 15 g/L cell dry weight.

21. A method according to claim 16, wherein the temperature is about 50° C.

22. A method according to claim 16, wherein glutamic acid is produced at a concentration of at least about 40 g/L.

23. A method according to claim 16, wherein glutamic acid is produced with a carbon conversion of methanol to glutamate of at least about 20%.

* * * * *

UNITED STATES PATENT AND TRADEMARK OFFICE
CERTIFICATE OF CORRECTION

PATENT NO.     : 6,083,728
DATED          : July 4, 2000
INVENTOR(S)    : Schendel et al.

It is certified that error appears in the above-identified patent and that said Letters Patent is hereby corrected as shown below:

<u>Title page,</u>
[75] Inventors: "Kawasaki" should read -- Kawasaki-shi --

<u>Column 1,</u>
Line 30: "5:243-252" should read -- 56:243-252 --
Line 40: "22:112-1117" should read -- 27:112-1117 --

<u>Column 3,</u>
Line 7: "439" should read -- 42:439 --

<u>Column 5,</u>
Line 44: "45-550° C" should read -- 45-55° C --
Line 66: "B12" should read -- $B_{12}$ --

<u>Column 9,</u>
Line 62: "0.03w" should read -- 0.03% --

<u>Column 10,</u>
Line 3: "calorimeter" shold read -- colorimeter --
Line 19: "40° C" should read -- 4° C --
Line 49: "1:195-206" should read -- 12:195-206 --

<u>Column 12,</u>
Line 56: "5.8x104" should read -- $5.8 \times 10^{-4}$ --

<u>Column 14,</u>
Line 61: "$2H_2O1$ mg" should read -- $2H_2O$ 1mg --

UNITED STATES PATENT AND TRADEMARK OFFICE
CERTIFICATE OF CORRECTION

PATENT NO. : 6,083,728
DATED : July 4, 2000
INVENTOR(S) : Schendel et al.

It is certified that error appears in the above-identified patent and that said Letters Patent is hereby corrected as shown below:

<u>Column 16,</u>
Line 27: "30 carbon" should read -- 30% carbon --

Signed and Sealed this

Twenty-fifth Day of September, 2001

Attest:

*Attesting Officer*

NICHOLAS P. GODICI
*Acting Director of the United States Patent and Trademark Office*